(12) United States Patent
Dennis et al.

(10) Patent No.: US 7,294,496 B1
(45) Date of Patent: Nov. 13, 2007

(54) CLONED HUMAN LYSOPHOSPHOLIPASE

(75) Inventors: Edward A. Dennis, La Jolla, CA (US); Aijun Wang, Sammamish, WA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/493,601

(22) Filed: Jan. 28, 2000

(51) Int. Cl.
*C12N 9/20* (2006.01)
*C12N 1/20* (2006.01)
*C12N 15/00* (2006.01)
*C07H 21/04* (2006.01)
*A61K 31/70* (2006.01)

(52) U.S. Cl. ............... 435/198; 435/252.3; 435/320.1; 536/23.2; 514/44

(58) Field of Classification Search .............. 435/198, 435/252.3, 320.1; 536/23.2; 514/44
See application file for complete search history.

(56) References Cited

U.S. PATENT DOCUMENTS 5,965,423 A * 10/1999 Hillman et al. ............. 435/198

OTHER PUBLICATIONS

Sequence search alignment between Applicants' SEQ ID No. 1 and Accession No. AF052112.*
Wang et al. [BBA 1437:157-169 (1999)].*

* cited by examiner

*Primary Examiner*—Tekchand Saidha
(74) *Attorney, Agent, or Firm*—DLA Piper US LLP

(57) ABSTRACT

A cloned of a human brain lysophospholipid-specific lysophospholipase enzyme molecule, its potential use for treatment of a host of diseases and method of inactivation are disclosed. Also disclosed are its distribution in tissue sand detailed kinetic analysis. hLysoPLA has a single substrate binding site and a surface recognition site. In contrast to many nonspecific lipolytic enzymes that exhibit lysophospholipase activity, hLysoPLA hydrolyzes only lysophospholipids and has no other significant enzymatic activity.

4 Claims, 10 Drawing Sheets

```
                                                          /NdeI
cDNA         CCGGGCGCCCGCTCTTCCTTCCGCTTGCGCTGTGAGCTGAGGCGGTGTATGTGCGGCAAT    60
amino acid                                                       M  C  G  N     4 cDNA         AACATGTCAACCCCGCTGCCCGCCATCGTGCCCGCCGCCCGGAAGGCCACCGCTGCGGTG   120
amino acid    N  M  S  T  P  L  P  A  I  V  P  A  A  R  K  A  T  A  A  V    24 cDNA         ATTTTCCTGCATGGATTGGGAGATACTGGGCACGGATGGGCAGAAGCCTTTGCAGGTATC   180
amino acid    I  F  L  H  G  L  G  D  T  G  H  G  W  A  E  A  F  A  G  I    44 cDNA         AGAAGTTCACATATCAAATATATCTGCCCGCATGCGCCTGTTAGGCCTGTTACATTAAAT   241
amino acid    R  S  S  H  I  K  Y  I  C  P  H  A  P  V  R  P  V  T  L  N    64 cDNA         ATGAACGTGGCTATGCCTTCATGGTTTGATATTATTGGGCTTTCACCAGATTCACAGGAG   300
amino acid    M  N  V  A  M  P  S  W  F  D  I  I  G  L  S  P  D  S  Q  E    84 cDNA         GATGAATCTGGGATTAAACAGGCAGCAGAAAATATAAAAGCTTTGATTGATCAAGAAGTG   360
amino acid    D  E  S  G  I  K  Q  A  A  E  N  I  K  A  L  I  D  Q  E  V   104 cDNA         AAGAATGGCATTCCTTCTAACAGAATTATTTTGGGAGGGTTTTCTCAGGGAGGAGCTTTA   420
amino acid    K  N  G  I  P  S  N  R  I  I  L  G  G  F  S  Q  G  G  A  L   124
                                                     *
cDNA         TCTTTATATACTGCCCTTACCACACAGCAGAAACTGGCAGGTGTCACTGCACTCAGTTGC   480
amino acid    S  L  Y  T  A  L  T  T  Q  Q  K  L  A  G  V  T  A  L  S  C   144 cDNA         TGGCTTCCACTTCGGGCTTCCCTTCCACAGGGTCCTATCGGTGGTGCTAATAGAGATATT   540
amino acid    W  L  P  L  R  A  S  L  P  Q  G  P  I  G  G  A  N  R  D  I   164 cDNA         TCTATTCTCCAGTGCCACGGGGATTGTGACCCTTTGGTTCCCCTGATGTTTGGTTCTCTT   600
amino acid    S  I  L  Q  C  H  G  D  C  D  P  L  V  P  L  M  F  G  S  L   184
                              *
cDNA         ACGGTGGAAAAACTAAAAACATTGGTGAATCCAGCCAATGTGACCTTTAAAACCTATGAA   660
amino acid    T  V  E  K  L  K  T  L  V  N  P  A  N  V  T  F  K  T  Y  E   204 cDNA         GGTATGATGCACAGTTCGTGTCAACAGGAAATGATGGATGTCAAGCAATTCATTGATAAA   720
amino acid    G  M  M  H  S  S  C  Q  Q  E  M  M  D  V  K  Q  F  I  D  K   224
                          *           EcoRI cDNA         CTCCTACCTCCAATTGATTGACGTCACTAAGAGGCCTT                          758
amino acid    L  L  P  P  I  D  *                                           230
```

|   | 1 | 2 | 3 | 4 | 5 | 6 | 7 | 8 |
|---|---|---|---|---|---|---|---|---|
| A | Whole Brain (8.0) | amygdala (5.0) | caudate nucleus (5.8) | cerebellum (18.0) | cerebral cortex (4.4) | frontal lobe (4.0) | hippocampus (9.6) | medulla oblongata (5.0) |
| B | occipital lobe (10.2) | putamen (9.2) | substantia nigra (10.9) | temporal lobe (6.7) | thalamus (17.0) | subthalamic nucleus (14.4) | spinal cord (11.2) | |
| C | heart (42.4) | aorta (10.7) | skeletal muscle (41.9) | colon (36.3) | bladder (17.9) | uterus (14.6) | prostate (30.8) | stomach (43.4) |
| D | testis (83.3) | ovary (10.8) | pancreas (31.9) | pituitary gland (16.3) | adrenal gland (46.5) | thyroid gland (25.6) | salivary gland (48.8) | mammary gland (22.8) |
| E | kidney (29.4) | liver (42.8) | small intestine (29.8) | spleen (31.0) | thymus (23.0) | peripheral leukocyte (21.2) | lymph node (23.0) | bone marrow (12.7) |
| F | appendix (15.0) | lung (21.8) | trachea (34.9) | placenta (100.0) | | | | |
| G | fetal brain (18.4) | fetal heart (38.4) | fetal kidney (51.5) | fetal liver (47.7) | fetal spleen (55.5) | fetal thymus (26.9) | fetal lung (42.4) | |
| H | yeast total RNA 100ng | yeast tRNA 100 ng | E. coli rRNA 100ng | E. coli DNA 100 ng | Poly r(A) 100ng | human Cot1 DNA 100ng | human DNA 100 ng (3.4) | human DNA 500 ng (8.8) |

C

CLONED HUMAN LYSOPHOSPHOLIPASE

BACKGROUND OF THE INVENTION

1. Field of the Invention

The present invention relates to enzymes that hydrolyze lysophospholipids in tissues.

The present invention particularly concerns a new, cloned human brain lysophospholipase, its kinetic parameters and of its potential role in treatment of disease states having elevated concentrations of lysophospholipids, including atherosclerosis, hyperlipidemia, lethal dysrhythmias in myocardial ischemia and segmental demyelination of peripheral nerves.

2. Description of Related Art

Lysophospholipases (LysoPLA) are important enzymes that hydrolyze lysophospholipids (LysoPL). LysoPLs are detergent-like intermediates in phospholipid metabolism and play essential roles in many physiological and pathological processes. Lysophosphatidylcholine (LysoPC), a normal constituent of cell membranes, may act as a lipid messenger, transducing signals initiated from membrane receptors. Exogenous addition of LysoPC to cultured cells regulates the expression and/or activity of a variety of proteins including nitric oxide synthase, IL-1β, transcription factor nuclear factor-kappa B, activator protein 1, c-Jun N-terminal kinase, heparin-binding epidermal growth factor-like growth factor, cellular adhesion molecule-1 and many other proteins. LysoPC also modulates intracellular Ca 2/levels, stimulates the release of arachidonic acid in human endothelial cells and rat mesangial cells through a pathway that involves the activation of PKC and cPLA2. Lysophosphatidic acid (LPA), the simplest natural occurring LysoPL, is a multifunctional phospholipid messenger that evokes a variety of biological responses, ranging from platelet aggregation to smooth muscle contraction, from cell proliferation and differentiation to focal adhesion assembly and stress fiber formation. Such diversified biological responses to LPA appear to involve the activation of a specific G-protein coupled receptor, which in turn couples to multiple independent effector pathways including the small GTP-binding proteins Ras and Rho. Indeed, LPA-specific receptors were cloned recently and identified as members of the G-protein coupled receptors. Increased LysoPL levels have been detected in a variety of disease states including atherosclerosis, hyperlipidemia, lethal dysrhythmias in myocardial ischemia and segmental demyelination of peripheral nerves. Accumulation of LysoPL can perturb the activities of many membrane-bound signal-transducing enzymes, distort cell membrane integrity and even lead to cell lysis.

These increased LysoPL levels are believed to result from the dysfunction of LysoPL-regulating enzymes. Since LysoPLs play such diversified roles, their levels must be strictly regulated for proper cell function and survival. LysoPLA, which controls LysoPL levels through hydrolysis, has been identified in a variety of cells and tissues. Recently, a rat and a mouse LysoPLA have been sequenced, cloned and expressed. These two enzymes (both of 25 kDa molecular mass) share high sequence homology and exhibit similar properties. They are new members of the K/L hydrolase family with a catalytic site composed of Ser-119, Asp-174 and His-208.

SUMMARY OF THE INVENTION

The present invention contemplates a cDNA segment encoding a lysophospholipid-specific human lysophospholipase enzyme protein molecule having 690 deoxyribonucleotide base pairs from position 48 to position 741 od SEQ ID NO: 1, as shown in FIG. 1, and modifications thereof that encode active human lysophospholipase molecules.

More preferably, the invention contemplates a deoxyribonucleic acid sequence for a cDNA segment encoding a lysophospholipid-specific human brain lysophospholipase enzyme protein molecule, having a sequence of 690 deoxyribonucleotide base pairs from position 48 to position 741 of SEQ ID NO: 1, as shown in FIG. 1, and modifications thereof that encode active human lysophospholipase molecules.

The present invention also contemplates a recombinant lysophospholipid-specific human brain lysophospholipase enzyme protein molecule, having a single 25 kDa polypeptide of 230 amino acid residues in length, and a catalytic activity site triad at Ser-119, Asp-174 and His-208, and active modifications thereof.

More preferably, an amino acid residue sequence for a recombinant lysophospholipid-specific human brain lysophospholipase enzyme protein molecule having amino acid residues from amino acid residue position 1 to amino acid residue position 230, of SEQ ID NO: 2, as shown in FIG. 1, and active modifications thereof.

The present invention further relates to a contemplated method of inhibiting catalytic activity of a recombinant lysophospholipid-specific human brain lysophospholipase enzyme protein molecule by exposing the lysophosphlipase enzyme protein molecule to a solution containing methyl arachidonyl fluorophospates.

In the most preferred embodiment, the inhibiting that results from the exposing is irreversible.

In another, most preferred embodiment, is contemplated a method for treating subjects with diseases cased by increased levels of lysophospholipids, the method comprising supplying a recombinant lysophospholidip-specific lysophospholipase enzyme to an enzyme-deficient subject. The method of supplying can be administered by infusion. More preferably, the supplying is by gene augmentation therapy.

Still further embodiments and advantages of the invention will become apparent to those skilled in the art upon reading the entire disclosure contained herein.

BRIEF DESCRIPTION OF THE DRAWINGS

FIG. 1 shows the cDNA (SEQ ID NO: 3) and translated amino acid (SEQ ID NO: 2) sequences of human brain LysoPLA. The cDNA and amino acid residues that are different between the human and mouse enzymes are in bold, the catalytic triad is marked by *. The primers that were used to clone the human enzyme are indicated by the lines above the cDNA sequences, and the sequences refer to the sequences in the experimental procedures. The 5' and 3' untranslated cDNA sequences were obtained from GenBank.

140 ng of recombinant human brain LysoPLA were added to the 1 U substrate to start the reaction at 40° C. for 2, 5 or 10 min. The specific activity of lysophospholipase for each substrate concentration was obtained from the activity (nmol/mg) vs. time plot. Data were fit to Michaelis-Menten equation (dotted line) and to Hill model (solid line). Each data point represents an average of three independent experiments, each in triplicate.

Figure 4A:
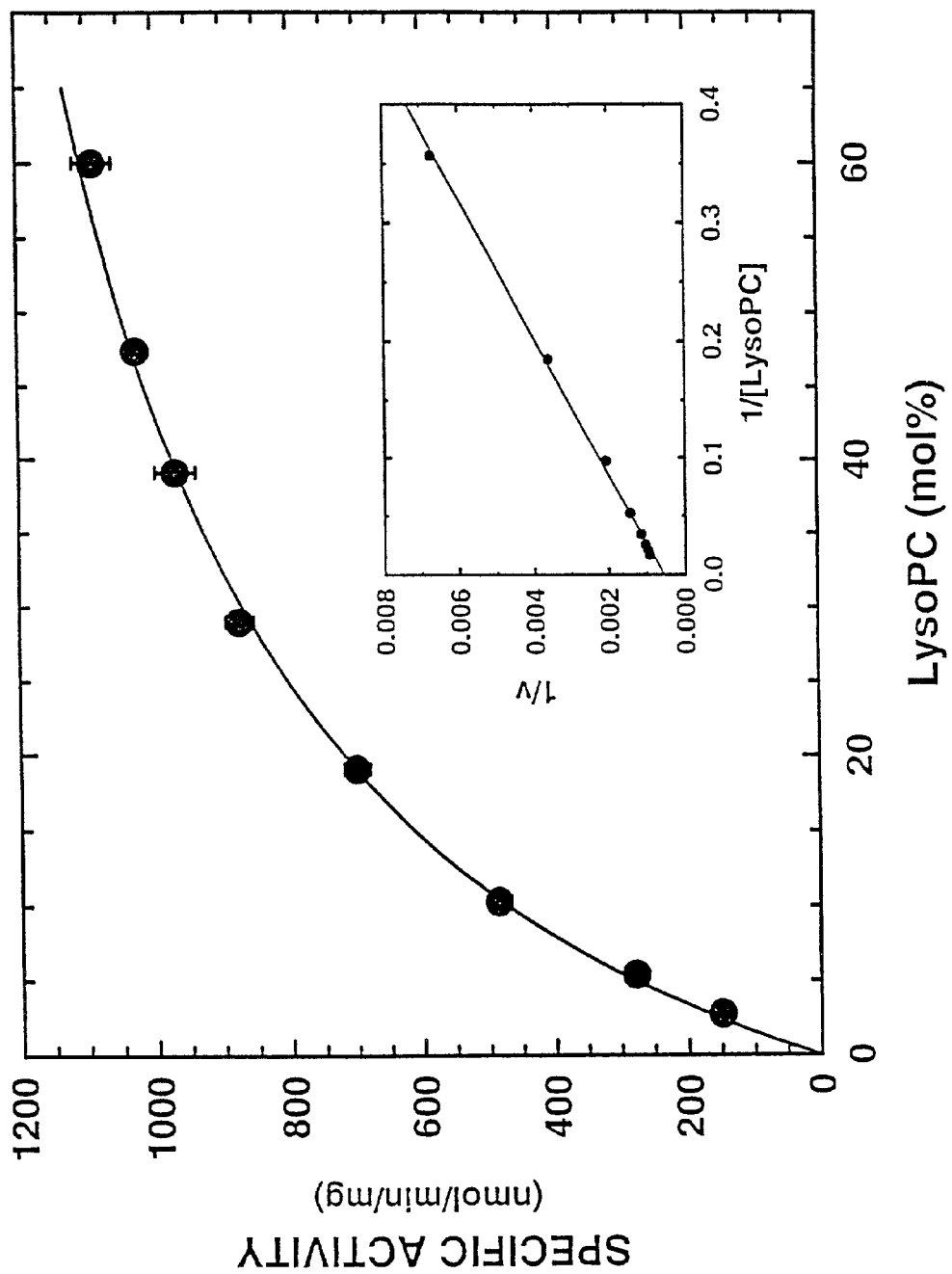
Figure 4B:
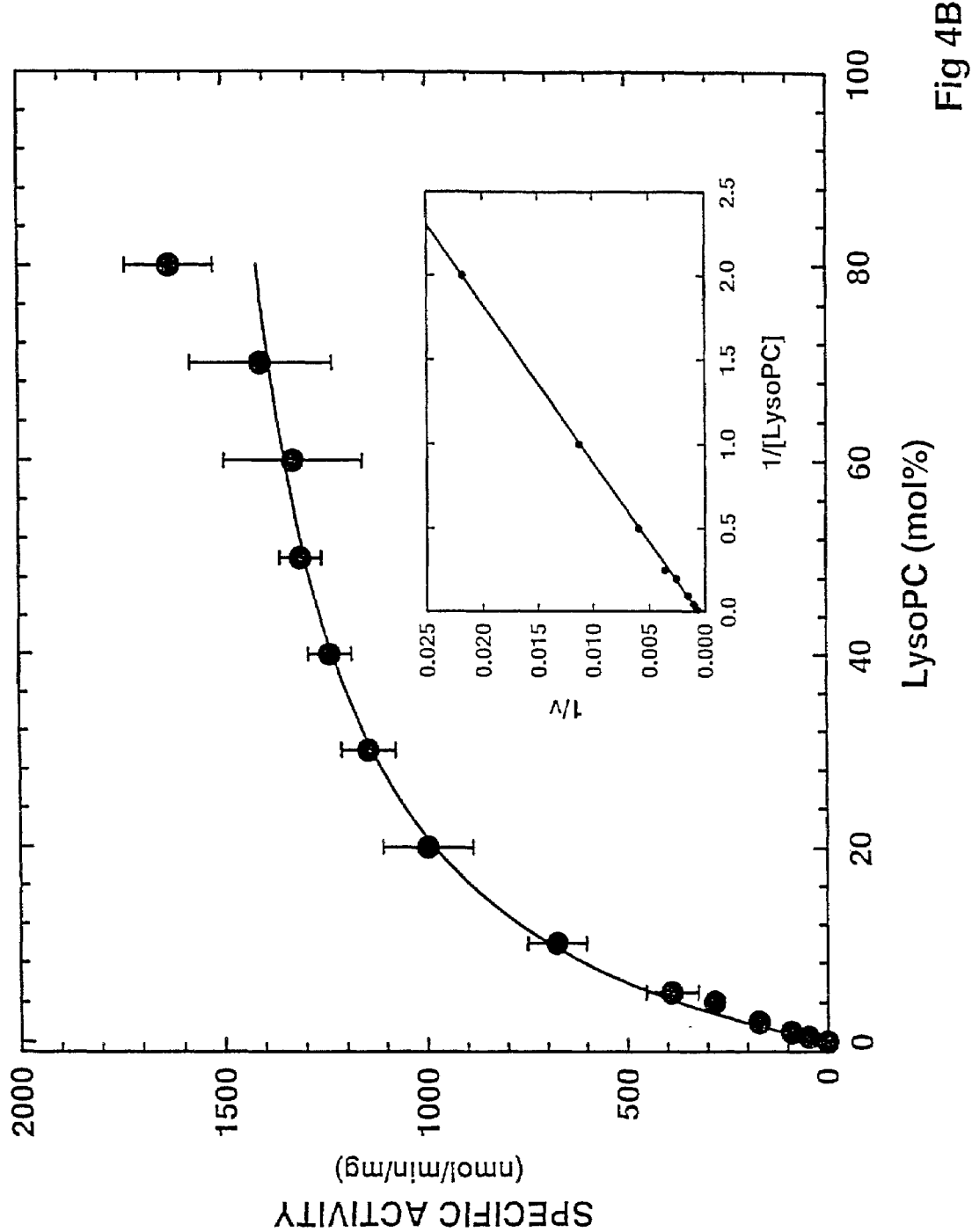
Figure 4C:
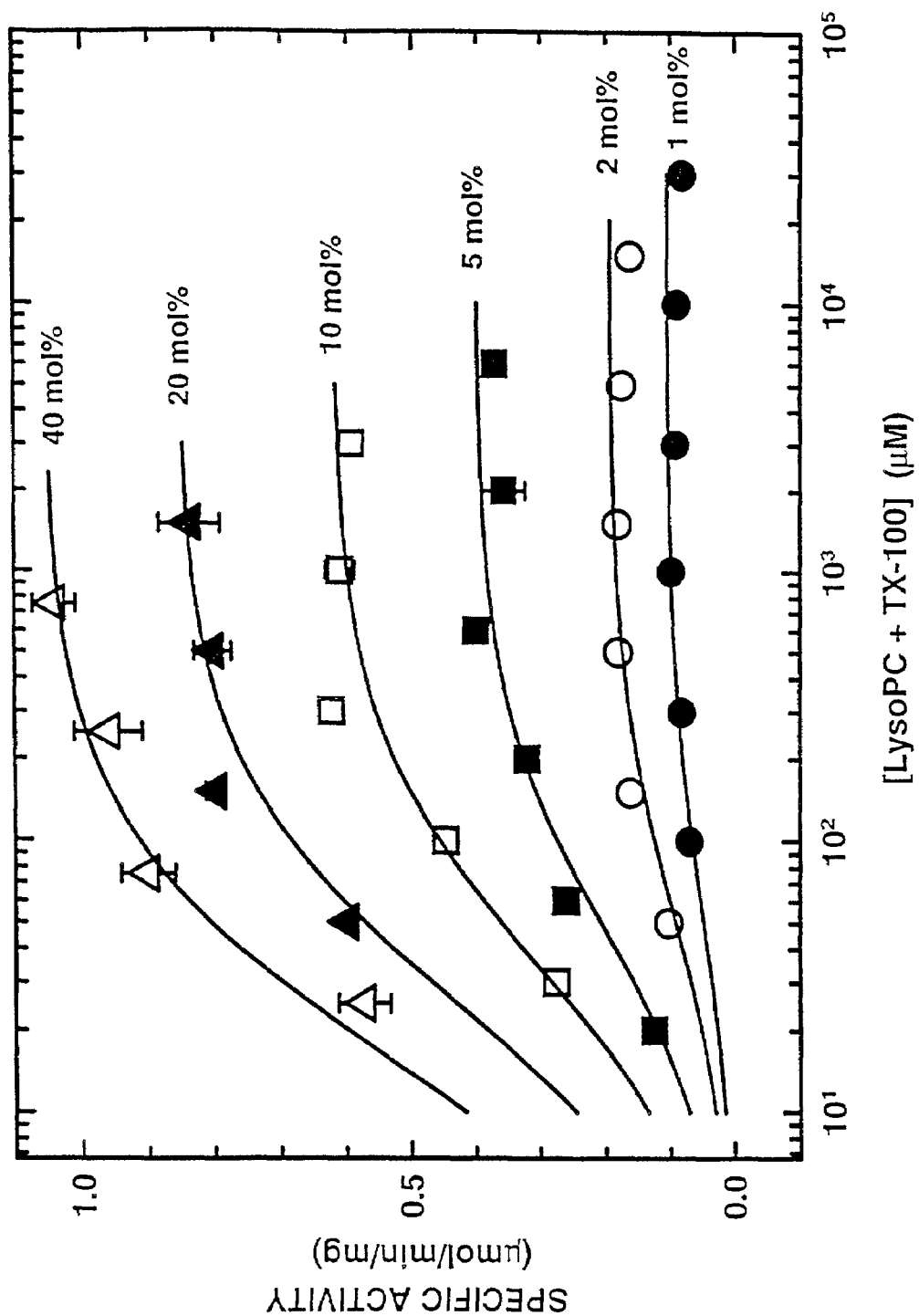

FIG. 4. is a kinetic analysis of human recombinant LysoPLA. LysoPLA activity was determined as a function of the mol % of LysoPC achieved either by fixing the LysoPC (1.125 mM) and varying the TX-100 concentration (A), or by fixing TX-100 (1 mM) and varying the LysoPC substrate concentration (B), or by fixing the mole fraction (surface concentration) of LysoPC, as indicated by the numbers in C. Each data point represents an average of four determinations in A, and an average of two independent experiments, each in triplicate in B and C. Data in A and B were fitted assuming Michaelis-Menten kinetics, and the inserts are the linear fits of the double reciprocal plots. Lines in C are the global fits using Equation 1.

Figure 5:
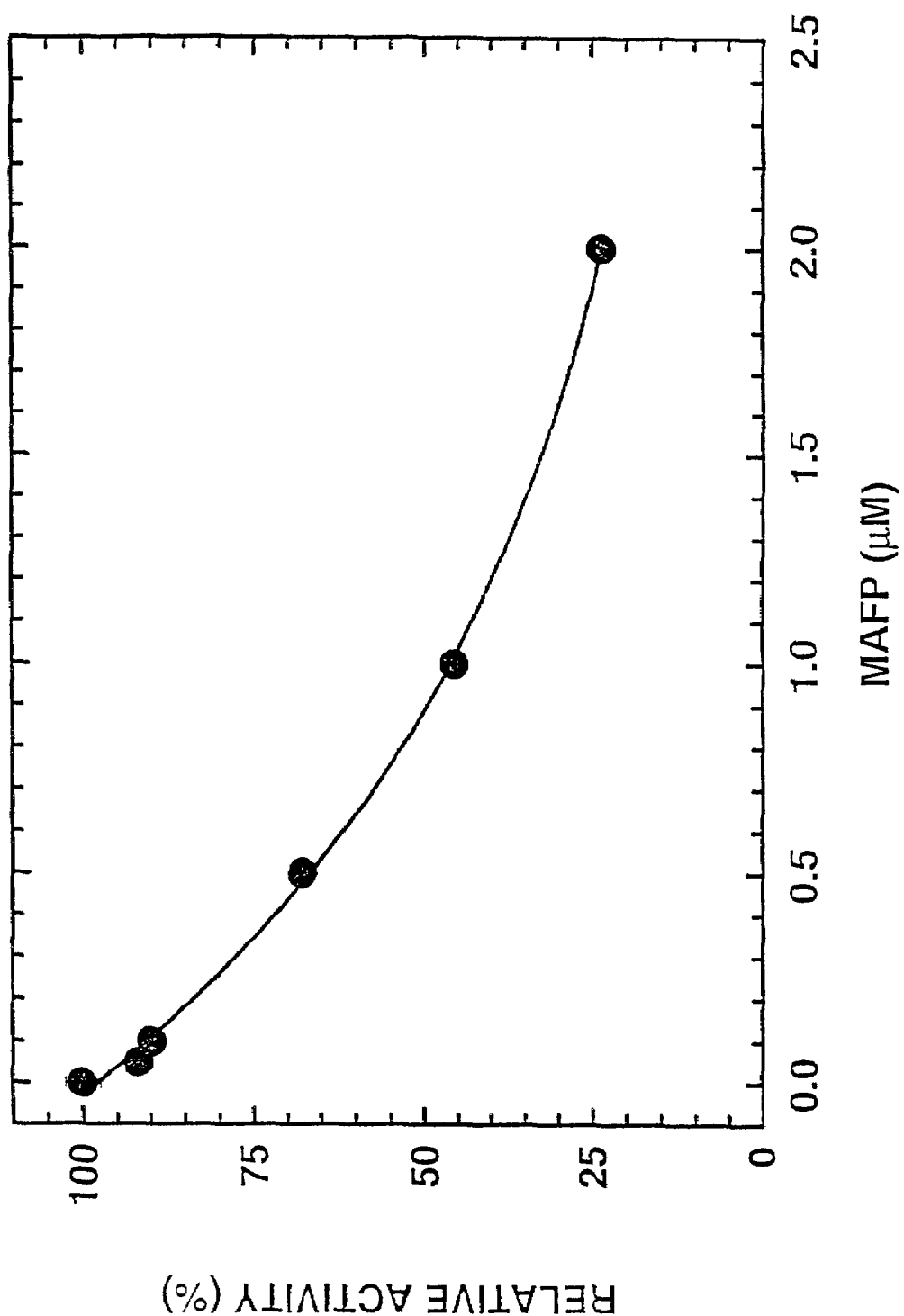

FIG. 5. demonstrates inhibition of human recombinant LysoPLA by MAFP. LysoPLA activity was assayed in the presence of different concentrations of MAFP, and expressed as percentage of the activity in the absence of the inhibitor. The data were fit to a single exponential decay.

Figure 6A:
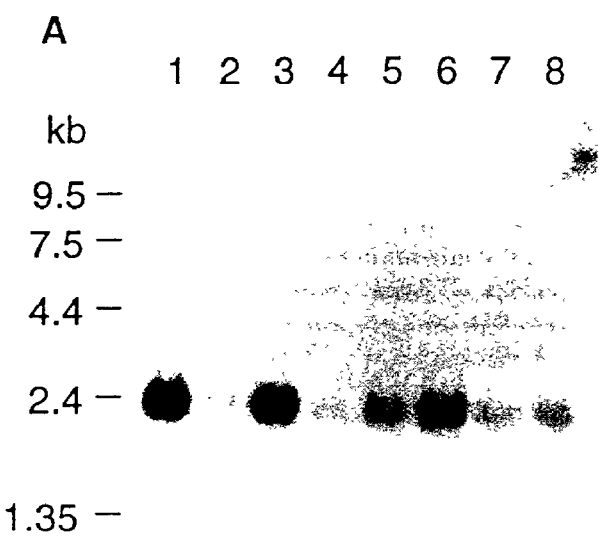

FIG. 6A. refers to the tissue distribution of human LysoPLA in the heart, brain, placenta, lung, liver skeletal muscle, kidney and pancreas (lanes 1-8 respectively).

Figure 6B:
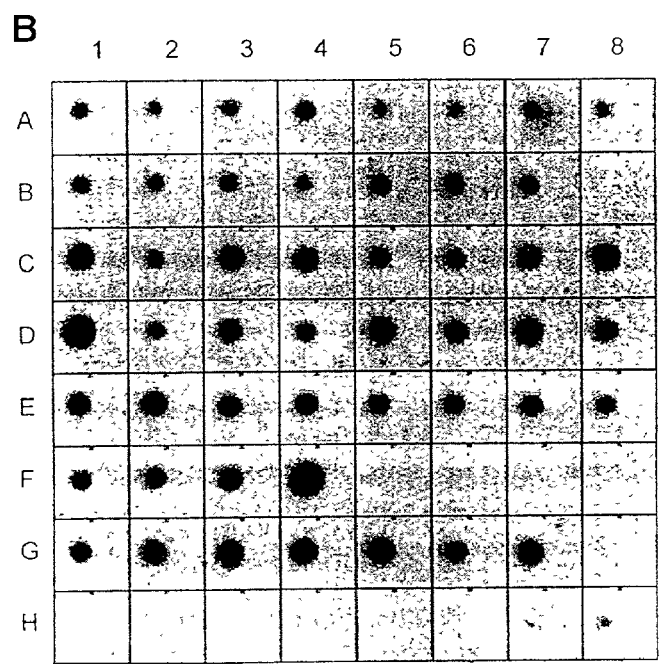

FIG. 6B. refers to the tissue distribution of human LysoPLA mRNA for more specific brain regions, glands and tissues shown in FIG. 6B.

FIG. 6C. refers to the textual description of the tissue distribution of human LysoPLA as exemplified in FIG. 6B.

Figure 6D:
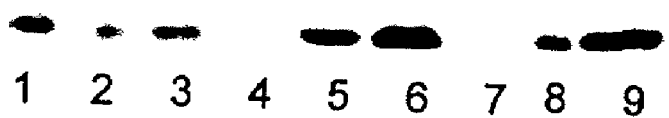

FIG. 6D. is a Western blot showing the protein levels of LysoPLA in 70μ of protein from human brain, heart, liver, lung kidney, testis, ovary and placenta (lanes 1-8 respectively) 5 ng of purified recombinant human LysoPLA is in lane 9 as a control.

DETAILED DESCRIPTION OF THE INVENTION

| Abbreviations | |
|---|---|
| BEL | bromoenol lactone; |
| BSA | bovine serum albumin; |
| cPLA2 | cytosolic Ca 2/-dependent phospholipase A2; |
| DPPC | 1-palmitoyl-2-palmitoyl-sn-glycero-3-phosphorylcholine; |
| hLysoPLA | human lysophospholipase; |
| iPLA2 | Ca 2/-independent phospholipase A2 |
| IPTG | isopropyl thio-L-D-galactoside; |
| LysoPC | 1-palmitoyl-sn-glycero-3-phosphorylcholine; |
| LysoPL | lysophospholipid; |
| Lme | L-mercaptoethanol; |
| MAFP | methyl arachidonyl £uorophosphonate; |
| mLysoPLA | mouse lysophospholipase; |
| PACOCF3 | palmitoyl tri£uoromethyl ketone; |
| PAPC | 1-palmitoyl-2-arachidonyl-sn-glycero-3-phosphorylcholine; |
| PCR | polymerase chain reaction; |
| PIP2 | phosphatidylinositol 4,5-bisphosphate; |
| PlsCho | plasmenylcholine (1-O-(Z)-1P-alkenyl-2-arachidonoyl-sn-glycero-3-phosphorylcholine); |
| TX-100 | Triton X-100 |

Definition of Terms

Amino Acid: All amino acid residues identified herein are in the natural L-configuration. In keeping with standard polypeptide nomenclature, *J. Biol. Chem.*, 243:3557-59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| L | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagin |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a radical such as H and OH (hydrogen and hydroxyl) at the amino- and carboxy-termini, respectively, or a further sequence of one or more amino acid residues up to a total of about fifty residues in the polypeptide chain specific.

Base Pair (bp): A partnership of adenine (A) with thymine (T), or of cytosine (C) with guanine (G) in a double stranded DNA molecule.

Constitutive promoter: A promoter where the rate of RNA polymerase binding and initiation is approximately constant and relatively independent of external stimuli. Examples of constitutive promoters include the cauliflower mosaic virus 35S and 19S promoters described by Poszkowski et al., *EMBO J.*, 3:2719 (1989) and Odell et al., *Nature*, 313:810 (1985).

DNA: Desoxyribonucleic acid.

Enzyme: A protein, polypeptide, peptide RNA molecule, or multimeric protein capable of accelerating or producing by catalytic action some change in a substrate for which it is often specific.

Expression vector: A DNA sequence that forms control elements that regulate expression of structural genes when operatively linked to those genes.

Expression: The combination of intracellular processes, including transcription and translation undergone by a structural gene to produce a polypeptide.

Insert: A DNA sequence foreign to the rDNA, consisting of a structural gene and optionally additional DNA sequences.

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide.

Operatively linked or inserted: A structural gene is covalently bonded in correct reading frame to another DNA (or RNA as appropriate) segment, such as to an expression vector so that the structural gene is under the control of the expression vector.

Polypeptide and peptide: A linear series of amino acid residues connected one to the other by peptide bonds between the alpha-amino and carboxy groups of adjacent residues.

Promoter: A recognition site on a DNA sequence or group of DNA sequences that provide an expression control element for a gene and to which RNA polymerase specifically binds and initiates RNA synthesis (transcription) of that gene.

Inducible promoter: A promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like.

Spatially regulated promoter: A promoter where the rate of RNA polymerase binding and initiation is modulated in a specific structure of the organism such as the leaf, stem or root. Examples of spatially regulated promoters are given in Chua et al., *Science,* 244:174-181 (1989).

Spatiotemporally regulated promoter: A promoter where the rate of RNA polymerase binding and initiation is modulated in a specific structure of the organism at a specific time during development. A typical spatiotemporally regulated promoter is the EPSP synthase-35S promoter described by Chua et al., *Science,* 244:174-181 (1989).

Temporally regulated promoter: A promoter where the rate of RNA polymerase binding and initiation is modulated at a specific time during development. Examples of temporally regulated promoters are given in Chua et al., *Science,* 244:174-181 (1989).

Protein: A linear series of greater than about 50 amino acid residues connected one to the other as in a polypeptide.

Recombinant DNA molecule: A hybrid DNA sequence comprising at least two nucleotide sequences not normally found together in nature.

RNA: Ribonucleic acid.

Selective Genetic marker: A DNA sequence coding for a phenotypical trait by means of which transformed cells can be selected from untransformed cells.

Structural gene: A DNA sequence that is expressed as a polypeptide, i.e., an amino acid residue sequence.

Synthetic promoter: A promoter that was chemically synthesized rather than biologically derived. Usually synthetic promoters incorporate sequence changes that optimize the efficiency of RNA polymerase initiation.

1. Introduction

This invention discloses the cloning, expression and purification of the human LysoPLA (hLysoPLA). The substrate specificity, kinetics and inhibition of pure hLysoPLA was examined. Recently, it was reported that a similar rabbit LysoPLA also functioned as a PLA2 to hydrolyze plasmenylcholine, which is abundant in heart and brain; this is not the case for the human enzyme. Furthermore, the tissue and regional distribution patterns of the enzyme have been characterized herein.

2. Experimental Design, Materials and Methods 2.1. Cloning of Human LysoPLA

Human brain messenger RNA (Clonetech) was used to synthesize first-strand cDNA at 37° C. for 1 h using Moloney murine leukemia virus reverse transcripts (Stratagene) and random primers (Promega). Aliquots of the first-strand cDNA were used to amplify the hLysoPLA gene by PCR using Taq DNA polymerase (Promega). The sequences of the primers used in the PCR cycles were: 5 P-GGG GGG CAT ATG TGC GGC AAT AAC ATG TCA ACC CC-3 P (SEQ ID NO: 4) and 5 P-GCG CGA ATT CTC AAT CAA TTG GAG GTA GGA GTT TAT-3 P (SEQ ID NO: 5). These primers were designed based on the human sequences found in the GenBank using the mouse LysoPLA sequences as the probe. Restriction enzyme sites (NdeI and EcoRI) were included near the 5 P-end to facilitate directional cloning (see FIG. 1).

The PCR cycles were performed by preheating at 95° C. for 1 min, then five cycles of denaturation at 95° C. for 45 s, annealing at 60° C. for 1 min and extension at 72° C. for 2 min. This was followed by 25 cycles of 95° C. for 45 s, 66° C. for 1 min and 72° C. for 2 min. Finally, the PCR product was extended at 72° C. for 10 min. The amplified PCR product was about 700 bp, and was purified from a 1% agarose gel using Wizard™ PCR Preps (Promega).

To clone the human gene, the purified PCR product was ligated into the pCR2.1 vector (Original TA Cloning Kit from Invitrogen) using T4 DNA ligase (Pharmacia) at 14° C. for 19 h. The ligase was heat-inactivated by incubating at 70° C. for 10 min. The ligation product was used to transform *Escherichia coli* INVKF P cells, and then plated on LB-Amp (100 μg/ml) with X-Gal. After incubation overnight at 37° C. and then 6 h at 4° C., several white colonies were selected for overnight cultures in LB-Amp (100 μg/ml). The plasmids prepared from the over-night cultures were screened by restriction enzyme analysis using EcoRI and NdeI (Pharmacia). A majority of the screened colonies contained the vector with the correct size insert. The DNA sequence of the insert was obtained using an automated DNA sequencer (Applied Biosystems 373 from Perkin-Elmer). To subclone hLysoPLA from the pCR2.1 vector into the protein expression vector pET28a(+) (Novagen), both the pET28a(+) and the pCR2.1/hLyso-PLA vectors were digested with NdeI and EcoRI, and then separated on 1% agarose gels. The bands corresponding to hLysoPLA (approx. 700 base pairs) and pET28(+) (approx. 5300 base pairs) were purified and ligated as described hereinabove. The ligation product was used to transform competent *E. coli* NovaBlue cells (Novagen), and the resulting colonies were screened. It should be noted that the cloned hLysoPLA has an extra 20 amino acids at the N-terminus of the protein, the sequence of which is shown in Sequence 1:

Sequence 1:

MGSSHHHHHHSSGLVPR↓GSH-hLysoPLA (SEQ ID NO: 6)

His Tag    thrombin site

As indicated above, the H is Tag can be removed by thrombin cleavage, leaving three extra amino acids at the N-terminus of the protein.

2.2. Expression and Purification of hLysoPLA Protein

The pET28a(+)/hLysoPLA was used to transform competent *E. coli* BL21(DE3) (Novagen), and a single colony was inoculated in an overnight culture in LB-kanamycin (50 μg/ml) medium. This overnight culture was then diluted 40-fold into Terrific broth-kanamycin (50 μg/ml) medium, and allowed to grow at 37° C. until the A600 nm reached 1. Then, IPTG (Fisher) was added to a final concentration of 0.4 mM and the cells were grown at 22° C. for an additional 5 h to induce foreign protein expression. Finally, the *E. coli* cells were centrifuged and the pellet was stored at 32° C. The purification procedures were carried out at 4° C., as described previously.

Briefly, the *E. coli* pellet was resuspended in lysis bujer (25 mM Tris-HCl, pH 8.0, 500 mM NaCl, 5 mM imidazole and 10 mM LMe) and digested by lysozyme (Sigma). The mixture was sonicated and centrifuged at 100,000 U g for 45 min. The supernatant was passed through a Ni-NTA column (Qiagen), the column washed with lysis bujer, and the protein Z eluted with elution buffer (25 mM Tris-HCl, pH 8.0, 500 mM NaCl, 250 mM imidazole and 10 mM LMe). The eluted hLysoPLA was then loaded onto a Sephadex G-75 (2.5 U 90 cm, Pharmacia) column equilibrated in buffer containing 10 mM each of Tris-HCl (pH 8.0), NaCl and LMe. The hLysoPLA that eluted from the G-75 column was essentially homogeneous. The H is W Tag was removed by digestion with biotinylated thrombin (Novagen) overnight at 4° C. The biotinylated thrombin was removed at the end of the digestion by streptavidin agarose (Novagen), and the cleaved H is W Tag removed by dialysis against 10 mM each of Tris (pH 8.0) and LMe. The enzyme was stored at 32° C. after glycerol was added to a final concentration of 50% and LMe to 10 mM.

2.3. Northern Blot

The 32 P-labeled probe was prepared by incubating 50 ng cDNA of hLysoPLA with 50 μCi [32 P]dCTP (DuPont-NEN) and Ready-To-Go DNA labeling beads (-dCTP) (Pharmacia Biotech) at 37° C. for 15 min, as described by the protocol supplied by the manufacturer. The 32 P-labeled cDNA probe was purified through a ProbeQuant G-50 microcolumn (Pharmacia Biotech). The human RNA blot (Clone-tech) was prehybridized with 20 ml of ExpressHyb solution (Clonetech, CA) containing 1 mg/ml salmon sperm DNA at 65° C. for 30 min. The RNA blot was hybridized with 5 ml of ExpressHyb containing 6 μg/ml of human Cot-1 DNA, 30 μg/ml of salmon sperm DNA, 0.2 U SSC (sodium chloride and sodium citrate) and 10 7 cpm of human lysophospholipase cDNA probe (with speciactivity of 1.5 U 10 9 cpm/μg) overnight at 65° C. After hybridization, the membrane washed once with 200 ml of 2 U SSC containing 1% SDS at 65° C. for 20 min, and twice with 0.1 U SSC containing 0.5% SDS at 55° C. for 20 min each. The membrane was exposed to X-ray film for 24 h at 37° C. After developing, the film was read with a densitometer and each dot was quantitated.

2.4. Western Blot

The tissue distribution pattern of hLysoPLA at the protein level was examined by Western blot analysis using rabbit antibody (customer-made by HTI BioProducts) raised against purified recombinant hLyso-PLA. First, 70 μg of protein from different human tissues (Clonetech) were separated by 12% SDS—PAGE along with prestained protein molecular weight markers (Bio-Rad) and pure hLysoPLA. The proteins in the gel were then transferred to a PVDF membrane (Millipore). To block any non-specific binding, the membrane was incubated first in 5% non-fat milk in PBS (phosphate-buiered saline), followed by rabbit pre-immune serum (1/1000 dilution with PBS containing 0.5% Tween 20 and 0.5% milk) for 1 h. The protein bands recognized by the preimmune serum were visualized and blocked by treating the membrane with horseradish peroxidase-conjugated protein A (Amersham) and VECTOR SG substrate kit for peroxidase (Vector Laboratories). Then, the membrane was probed with the rabbit anti-hLysoPLA serum (1/1000 dilution) for 1 h, followed by horseradish peroxidase-conjugated protein A (Amersham). Finally, the protein bands were detected by the ECL system (Amersham).

2.5. LysoPLA Activity, PLA2 Activity and Protein Purity Determination

The protein concentration was determined by the Bio-Rad protein assay, using bovine serum albumin (BSA) as standard. Protein purity was examined using 12% SDS-PAGE and Coomassie blue staining. LysoPLA activity was measured at 40° C. in the assay buier containing LysoPC, 100 mM Tris-HCl (pH 8.0) and 10 mM LMe. Cold 1-palmitoyl-sn-glycero-3-phosphorylcholine (125 μM, unless indicated otherwise) was mixed with 1-[14 C]palmitoyl-sn-glycero-3-phosphorylcholine (100,000 cpm) in a total volume of 0.5 ml. The assay was initiated by adding an aliquot of enzyme solution to the substrate mixture and incubating for the desired time. The released fatty acid was extracted by the modified Dole method and then quantified by scintillation counting. The PLA2 activity assay was carried out, using various $^{14}$C-labeled phospholipid substrates under various conditions as given in the text. The rat brain iPLA2 was purified as described elsewhere (H. C. Yang et al., manuscript in preparation incorporated herein). Human recombinant cPLA2 was a gift from Drs. J. D. Sharp and R. M. Kramer at Lilly Laboratories. 1-[$^{14}$C]Palmitoyl-sn-glycero-3-phosphorylcholine and 1-palmitoyl-2-[1-$^{14}$C]palmitoyl-sn-glycerol-3-phosphorylcholine were purchased from Amersham. 1-Palmitoyl-2-[1-$^{14}$C]arachidonoyl-sn-glycerol-3-phosphorylcholine was purchased from DuPont-NEN. All unlabeled phospholipids were purchased from Avanti Polar Lipids. Triton X-100 (TX-100) and PIP2 were obtained from CalBiochem.

2.6. Synthesis of Plasmenylcholine

The sn-2 labeled PlsCho (plasmenylcholine or 1-O—(Z)-1P-alkenyl-2-arachidonoyl-sn-glycero-3-phosphocholine) was synthesized as follows. A total of 4 μmol [1-14C] arachidonic acid (from NEN, with specific activity 63.3 μCi/mol) was diluted 10 times with cold arachidonic acid in 250 μl distilled methylene chloride (Fisher Scientific). To this 0.04 mmol p(N,N-dimethyl)amino pyridine (Aldrich) and 0.08 mmol 1,3-dicyclohexyl carbodiimide (Aldrich) were added to yield the arachidonoyl anhydride upon 1 h of stirring. Lysoplasmenylcholine (0.06 mmol, from Serdary) dissolved in 200 μl methylene chloride and 50 μl pyridine (Fisher Scientic) was added to the arachidonoyl anhydride solution with 0.03 μmol dimethylaminopyridine and left stirring for 8 h. The reaction progress was monitored by thin layer chromatography (Merck) using a mobile phase of chloroform:methanol:triethyl amine:water (65:30:1.5:3.5), and retardation factors were 0.6 and 0.2 for PlsCho and LysoPlsCho, respectively. The separation of the product was carried out by preparative layer chromatography (Merck) in the above mobile system. The reaction yielded a total of 3.6 mg (7.7 μmol) of radiolabeled PlsCho (specific activity 0.18 μCi/μmol) by quantitative phosphate analysis.

2.7. Inhibition Studies of hLysoPLA

Various concentrations of each inhibitor (BioMol) were prepared in DMSO. 5 μl of each inhibitor was added to 480 μl of LysoPC substrate (125 μM Ly-soPC in the assay buffer). Enzyme (either mouse or human PLA) was added to the substrate-inhibitor mixture to start the reaction, which was incubated at 40° C. for 30 min. Control experiments were performed with the same amount of enzyme with 5 μl DMSO in the incubation mixture. The reversibility of the inhibition was tested by pre-incubation of the enzyme in the presence or absence of the inhibitor, followed by overnight dialysis in the assay buffer. The recovery of the enzyme activity as a function of time was then followed. Each data point represents an average of duplicates.

EXAMPLE 1

Cloning and Expression of hLysoPLA.

LysoPLA plays important roles in regulating the level of the multifunctional LysoPL, and several lines of evidence have suggested that LysoPLA exists in human. First, a relatively high level of LysoPLA activity has been found in human brain and it was proposed to be the major route by which LysoPL is removed from cell membranes [43]. Second, two human LysoPLAs (molecular masses of 20 and 22 kDa) have been puried from human HL-60 cells [55]. These two enzymes appear to be the human isoforms of the mouse 27 and 28 kDa LysoPLAs. Third, when we searched DNA and protein databases in GenBank using mouse LysoPLA sequence information, several human cDNA clones were identified that match to different parts of the mouse gene Wang et al./Biochimica et Biophysica Acta 1437 (1999) 157^169 with high homology. However, these cDNA sequences were obtained from different human tissues, their functions not identified, and none of them contained the entire protein sequence.

To determine the sequence of the human LysoPLA and to study the properties and functions of this enzyme in lipid metabolism and signal transduction, we have cloned this hLysoPLA using RT-PCR techniques. Normal human brain mRNA was used to generate the first-strand cDNA, from which a 700 bp product was amplified using primers corresponding to the N and C-terminals of hLysoPLA (FIG. 1). Then, the 700 bp DNA was ligated to the pCR2.1 vector and sequenced, as shown in FIG. 1 along with the translated protein sequences. The hLysoPLA is a single polypeptide composed of 230 amino acids with a calculated molecular mass of 25 kDa. The hLysoPLA sequence is highly homologous to the mouse/rat LysoPLA, 89% on the DNA level, and 92% on the protein level. The altered nucleotides and amino acids (shown in bold in FIG. 1) are spread out over the entire sequence, probably due to the random mutations of an ancestor enzyme during evolution. The Ser-119, Asp-174 and His-208 triad that forms the catalytic site for the mLysoPLA [46] is preserved in the human enzyme, indicating that the catalytic mechanism is also conserved.

Figure 2:
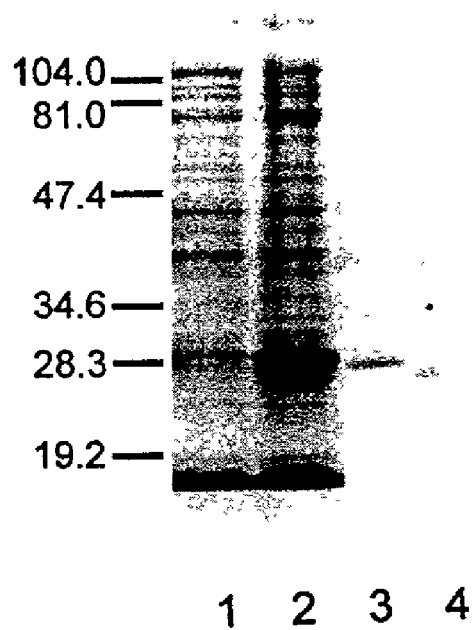
FIG. 2. is a depiction of SDS-PAGE of human brain. LysoPLA. Human recombinant LysoPLA (28 kDa) was strongly induced by IPTG in *E. coli* transformed with PET28a+/hLysoPLA (lane 2), as compared to that of *E. coli* before IPTG induction (lane 1). Lane 3 is the purified human recombinant LysoPLA with the His•Tag attached, and lane 4 shows the protein with the His•Tag removed by thrombin digestion as demonstrated by the protein band shift.

To express hLysoPLA, E. coli transformed with the protein expression vector pET28a(+)/hLysoPLA was induced with 0.4 mM IPTG. SDS-PAGE analysis of cell homogenates showed that a 28 kDa protein band is strongly induced (lane 2 vs. lane 1 in FIG. 2). The recombinant protein was purified in two steps. The first was Ni-NTA chromatography that removed the vast majority of the contamination proteins, and the second was G-75 chromatography that removed the minor high molecular weight contamination and exchanged the enzyme into a low salt buffer in which it is more stable. The hLysoPLA thus obtained was homogeneous as estimated by the SDS-PAGE (lane 3 in FIG. 2). The His-Tag at the N terminus of the protein was removed by thrombin, as shown in lane 4 of FIG. 2. The recombinant hLysoPLA thus obtained has an extra three amino acid residues (namely, Gly-Ser-H is) at the N terminus. The specific activity of the recombinant hLysoPLA is about 1.3 μmol/min/mg toward palmitoyl LysoPC, which is the same as the value reported for the 27 kDa mLysoPLA. This demonstrates that the sequence shown in FIG. 1 does indeed encode an active human LysoPLA.

EXAMPLE 2

Kinetic Characterization of the Recombinant hLysoPLA

Figure 3:
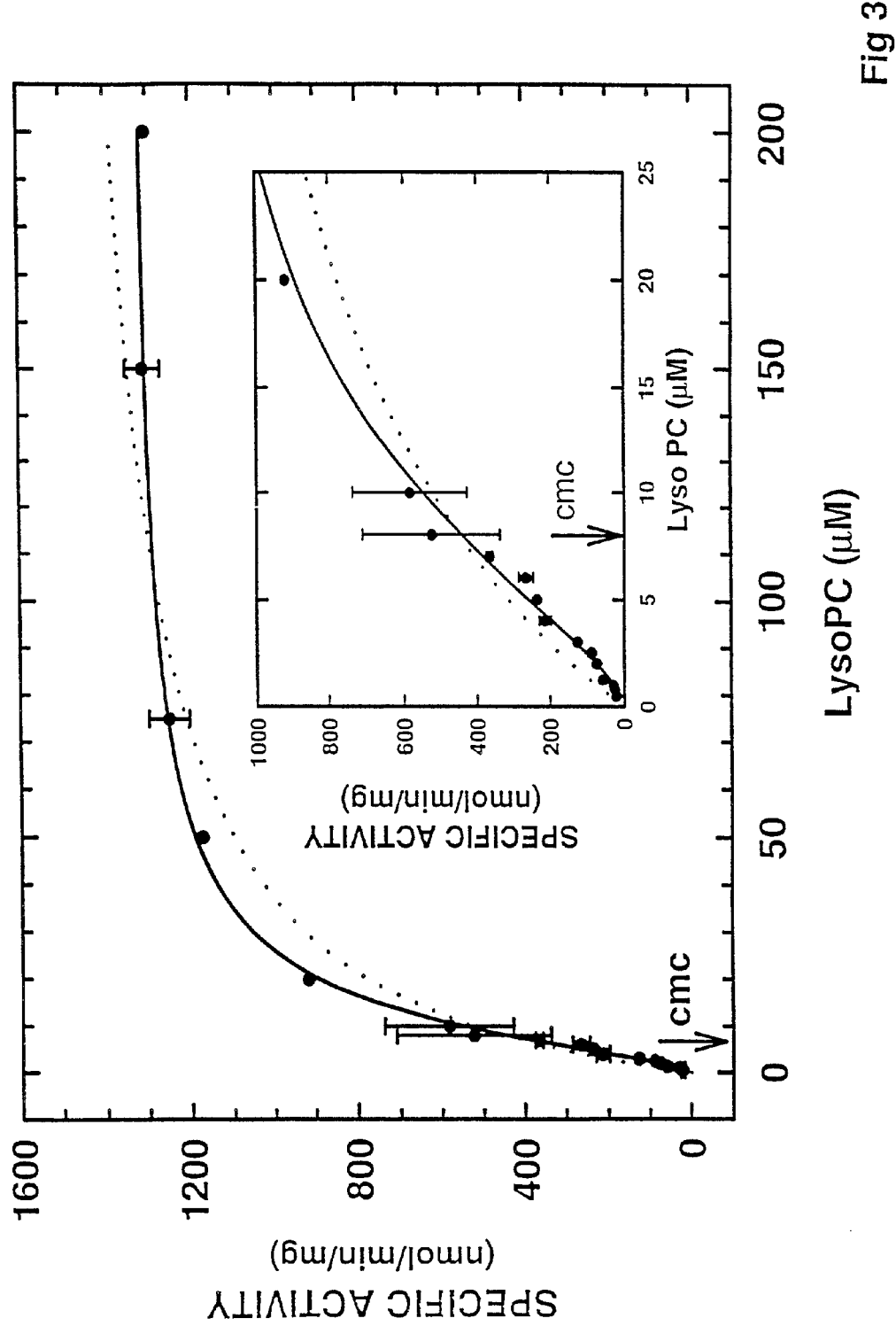
FIG. 3. demonstrates the activity of human LysoPLA as a function of LysoPC concentration. The substrate was prepared as a 20 U concentrated suspension, then diluted in the assay buffer to the desired final concentration, as indicated.

To investigate the catalytic properties of the hLy-soPLA, we first determined the specific activity of hLysoPLA as a function of substrate (1-palmitoyl LysoPC) concentration. As shown in FIG. 3, the catalytic activity exhibits saturation kinetics. However, the data did not fit well to the Michaelis-Menten equation (dotted line in FIG. 3). There seems to be some cooperativity, since the data fit to the Hill equation (solid line in FIG. 3) with n=1.53 þ0.08, kcat=1.34 þ0.04 μmol/min/mg, and substrate at half-maximal saturation is 12.7±0.9 μM. Furthermore, there is no dramatic increase in the enzyme activity near the cmc of the substrate (7 μM), indicating that the enzyme hydrolyzes both monomeric and micellar substrates. This suggests that hLysoPLA is not an interfacially activated enzyme.

TX-100 is often used in the purification and stabilization of membrane-associated proteins. In addition, it is used to change the surface concentration of the substrate in the mixed-micelle assay for mechanistic studies [56,57]. To determine the dependence of the enzyme activity on the substrate surface concentration, we measured the hLysoPLA activity under two conditions:

(1) the bulk LysoPC concentration (1.125 mM) was kept constant and the TX-100 concentration was varied (FIG. 4A);

(2) the bulk TX-100 concentration (1 mM) was kept constant and the LysoPC concentration was varied (FIG. 4B).

In both cases, enzyme activity increases as the percentage of LysoPC substrate in the micelles increases, and both sets of data fit well to the Michaelis-Menten equation with similar values of kcat (1.6 μmol/min/mg and 1.7 μmol/min/mg). These kcat values are also very close to that obtained in FIG. 3, a result expected if TX-100 serves as a neutral surface diluter of the substrate.

In addition, we have carried out detailed kinetic measurements and analysis to test the surface dilution kinetic model and results are shown in FIG. 4° C. The experimental data were fitted globally to Eq. 1 derived from the model in which hLysoPLA follows the two-step binding kinetics (Scheme 1). That is, hLysoPLA (E) binds first to the mixed-micellar surface (S) and then to the LysoPC substrate (A) presented on the surface.

Scheme 1:

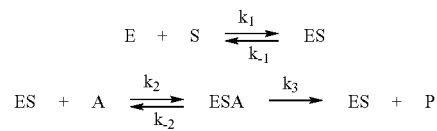

Equation 1:

$$v = \frac{V_{max}[LysoPC+TX-100]\{LysoPC\}}{K_m K_s + K_m[LysoPC+TX-100] + [LysoPC+TX-100]\{LysoPC\}}$$

Here, [LysoPC+TX-100] is the total molar concentration in the bulk solution, and {LysoPC®} is the molar fraction of the substrate on the mixed-micellar surface. Calculation of the amount of TX-100 in the micelle takes into account the amount of monomeric detergent in the solution, assuming the critical micelle concentration of TX-100 is 0.25 mM. The fitting parameter Ks represents the dissociation constant (k31/k1) for the mixed-micellar surface, Km represents the apparent Michaelis constant (=(k3+ k32)/k2) on the surface, and Vmax is the catalytic turnover rate. The values of parameters obtained from global fits are: Vmax=1.37±0.05 µmol/min/mg, Km=12.2±0.9 mol % and Ks=66±7 µM. These data are consistent with the following three conclusions.

First, the fact that a single value for Ks fits all the experimental data suggests that this enzyme binds to mixed-micelles with the same affinity regardless of the micellar composition.

Thus, the first binding step is likely to occur through a non-specific hydrophobic interaction with the surface. Second, the enzyme appears to act primarily on the substrate within the interface. This conclusion is also supported by surface dilution kinetics observed in FIGS. 4A and 4B. Third, the dependence of apparent Vmax on mol % of LysoPC in the micelle is consistent with a single binding site for the substrate. This 1:1 stoichiometry of substrate-enzyme complex suggests that the apparent cooperativity seen in the kinetics of hLysoPLA on pure LysoPC micelles (FIG. 3) results from the change in the substrate presentation (monomers vs. premicellar aggregates vs. micelles) rather than a cooperative binding of two or more substrates to catalytic or allosteric sites.

EXAMPLE 3

Insignificant PLA2 Activity of hLysoPLA

When we first purified the mouse LysoPLA from P388D1 cells, no other enzymatic activities (PLA1, PLA2, acyltransferase, transacylase and esterase) were found. Therefore, it appears to be a LysoPL-specific LysoPLA. Similar results were obtained for the rat LysoPLA and the relative rates towards different LysoPL substrates were reported [Sugimoto et al., (1996) J. Biol. Chem. 271, 7705-11]. However, a recently sequenced rabbit enzyme that shares high sequence homology (approx. 97%) to the rat/mouse LysoPLA was reported to have both PLA2 and LysoPLA activities [Portilla, et al., (1968) J. Am. Soc.Nephrol. 9, 1178-86]. The specific activities, however, were only 10 nmol/min/mg for PLA2 activity and 20 nmol/min/mg for LysoPLA activity. The PLA2 activity was also reported to be selective for PlsCho substrate with arachidonic acid at the sn2 position. To determine whether hLysoPLA also expresses PLA2 activity, we have explored its ability to hydrolyze arachidonic acid labeled PlsCho as well as other phospholipid substrates under a variety of conditions. As summarized in Table 1, hLysoPLA did not show any significant activity toward the PlsCho substrate labeled with [14 C]arachidonic acid, whether in mixed micelles or in vesicles. Also no PLA2 activity was found for hLysoPLA toward several phosphatidylcholine substrates.

As a control, LysoPLA activity toward LysoPC was determined at the same time with the same batch of enzyme. Since the hLysoPLA was active toward LysoPC, the insignificant PLA2 activity of hLysoPLA is not due to the inactivation of the enzyme. In comparison, cPLA2 (an arachidonic acid-selective PLA2) showed a relatively high activity toward PlsCho when the substrate was presented in the presence of 3 mol % PIP2, which is about 60% of its activity toward PAPC under the same conditions. Rat brain iPLA2 demonstrated a weak but significant activity toward PlsCho. It is 10- and 4-fold lower than its activity toward DPPC and PAPC TX-100 mixed micelles, respectively.

Because hLysoPLA did not show any significant activity toward any diradylglycerophospholipids (PlsCho, PAPC, DPPC) under all the conditions tested, the hLysoPLA is not a PLA2. In light of the high sequence homology among the mouse, rat and human LysoPLAs, and the fact that these enzymes exhibited the same kinetic properties, we propose that these LysoPLAs, as a group, are specific LysoPLAs without other significant enzymatic activities. The rabbit enzyme was originally reported to be only a PLA2 without any significant LysoPLA activity [Portilla et al., (1996) J. Biol. Chem. 271, 15451-57], and only recently was the LysoPLA activity found after the enzyme showed high sequence homology to the rat/mouse LysoPLA. The specific activity of the rabbit enzyme as a LysoPLA, however, was more than 50-fold lower than the specific activity of the corresponding mouse, rat and human enzymes under similar assay conditions. We have found several factors that can reduce the LysoPLA activity significantly and may contribute to the lower LysoPLA observed for the rabbit enzyme. For example, LysoPLA appears to be quite unstable and the temperature/solution components of the enzyme during purification, storage and assay affect its activity substantially. The percentage of hydrolysis and linearity of the reaction also need to be considered when the activity is determined from a single time point measurement. Because of the sequence homology between the rabbit enzyme and the human, rat and mouse LysoPLAs, the rabbit enzyme may be a LysoPL-specific LysoPLA as well.

EXAMPLE 4

Inhibition of the LysoPLA

Several small organic compounds were examined for their abilities to inhibit the mouse and human LysoPLA, and similar results were found for both enzymes. PACOCF3 and BEL are iPLA2 inhibitors, but neither of them inhibited the LysoPLA activity well. LysoPAF, a LysoPC substrate analog with an ether linkage in the sn-1 position, was not a good inhibitor either. MAFP is an inhibitor of both iPLA2 and cPLA2. Here, we found that it also inhibited LysoPLA with an apparent IC50 of 0.6 µM (FIG. 5). The inhibition of LysoPLA by MAFP is irreversible, since LysoPLA remained inactive when the enzyme and MAFP mixture was assayed after overnight dialysis. The inhibition of LysoPLA by MAFP is most likely due to the covalent modification of the enzyme at the active site Ser-119.MAFP has been used in signal transduction studies as a selective cPLA2 inhibitor. However, as it also inhibits both LysoPLA and iPLA2 activities, the contribution of each of these enzymes to signal transduction should be more carefully considered.

TABLE I

Substrate selectivity of lysophospholipase compared with cPLA$_2$ and iPLA$_2$ toward plasmenylphosphatidylcholine and phosphatidylcholine under various conditions. As a control, LysoPLA activity toward the LysoPC substrate was also included.

| Enzyme | Substrate | Assay conditions | Activity (μmol/min/mg) |
|---|---|---|---|
| Human Recombinant LysoPLA | LysoPC micelles (125 μM) | 100 mM Tris, pH 8.0, 10 mM βMe | 1.13 ± 0.03 |
| | PisCho/TX-100 mixed micelles (100 μM:600 μM) | 100 mM Hepes, pH 7.5, 10 mM βMe | 0.0024 ± 0.0004 |
| | PisCho sonicated vesicles (100 μM) | 100 mM Tris, pH 8.0, 4 mM EGTA, 10 mM βMe | 0.0009 ± 0.0003 |
| | PisCho sonicated vesicles (100 μM) | 100 mM Tris, pH 8.0, 150 mM NaCl, 3 mM MgCl$_2$, 10 mM βMe | 0.0006 ± 0.0002 |
| | DPPC/TX-100 mixed micelles (100 μM:400 μM) | 100 mM Hepes, pH 7.5, 2 mM DTT, 5 mM EDTA | <0.0001 |
| | DPPC/POPS sonicated vesicles (67 μM:33 μM) | 100 mM Hepes, pH 7.5, 5 mM EDTA or Ca$^{2+}$, 1 mg/ml BSA | <0.0001 |
| | PAPC/TX-100 mixed micelles (100 μM:400 μM) | 100 mM Hepes, pH 7.5, 80 μM Ca$^{2+}$, 2 mM DTT, 0.1 mg/ml BSA | <0.0001 |
| | PAPC/PIP$_2$/TX-100 mixed micelles (97 μM:3 μM:400 μM) | 100 mM Hepes, pH 7.5, 80 μM Ca$^{2+}$, 2 mM DTT, 0.1 mg/ml BSA | <0.0001 |
| Human Recombinant cPLA$_2$ | PisCho/PIP$_2$/TX-100 mixed micelles (100 μM:3 μM:600 μM) | 100 mM Hepes, pH 7.5, 80 μM Ca$^{2+}$, 0.1 mg/ml BSA, 2 mM DTT. | 13.58 ± 0.05 |
| | PAPC/PIP$_2$/TX-100 mixed micelles (97 μM:3 μM:400 μM) | 100 mM Hepes, pH 7.5, 80 μM Ca$^{2+}$, 0.1 mg/ml BSA, 2 mM DTT. | 21.81 ± 0.09 |
| Rat brain iPLA$_2$ | PisCho/TX-100 mixed micelles (100 μM:600 μM) | 100 mM Hepes, pH 7.5, 5 mM EDTA, 2 mM DTT | 0.53 ± 0.03 |
| | DPPC/TX-100 mixed micelles (100 μM:400 μM) | 100 mM Hepes, pH 7.5, 5 mM EDTA, 2 mM DTT | 5.6 ± 0.2 |
| | PAPC/TX-100 mixed micelles (100 μM:400 μM) | 100 mM Hepes, pH 7.5, 5 mM EDTA, 2 mM DTT | 2.0 ± 0.04 |

EXAMPLE 5

Tissue Distribution of hLysoPLA

To examine the tissue distribution pattern of LysoPLA, we have carried out Northern and Western blots using either the human LysoPLA gene as a Northern blot probe, or the rabbit antibody raised against pure recombinant hLysoPLA. As shown in FIG. 6A, the size of hLysoPLA messenger is about 2.4 kb. The mRNA is widely distributed in many tissues, with heart, placenta and skeletal muscle being the most abundant ones, followed by liver, pancreas, kidney, brain and lung. On the Northern master blot which has messengers from more tissues(FIGS. 6B,C), similar patterns were observed though the relative intensity for a few tissues was changed compared to FIG. 6A. In FIGS. 6B,C, placenta and testis are the most abundant sources for hLysoPLA, followed by adrenal and salivary glands, liver, heart, skeletal muscle, and trachea colon. In contrast to the mRNA levels in adult tissues, the fetal mRNA of hLysoPLA appears to be much more uniform among different tissues. To screen the expression of hLysoPLA in different tissues, Western analysis was performed with rabbit polyclonal antibody for the hLysoPLA. As shown in FIG. 6D, testis expressed the most abundant hLysoPLA, followed by kidney, brain, placenta, liver, heart and ovary.

Discussion

These examples define a new, cloned, expressed and characterized human lysophospholipid-specific LysoPLA. The enzyme is widely distributed in almost all tissues at both mRNA and protein levels, although the relative amount varies greatly from tissue to tissue. The human LysoPLA is homologous to the rat, mouse and rabbit enzymes, with the catalytic triad conserved in all and the changed residues spread randomly along the protein sequences. The mouse and human enzymes exhibit similar inhibition patterns toward various inhibitors, with MAFP being the most potent one. Detailed kinetic analysis shows that the human LysoPLA displays apparent co-operativity and surface dilution kinetics. The enzyme appears to bind nonspecifically to the mixed-micellar surface first, followed by the specific binding to the substrate on the surface.

The kinetic parameters associated with this surface dilution kinetic model were determined, and it appears that hLysoPLA has a single substrate binding site and a surface nonspecific recognition site. The apparent co-operativity is likely due to the change of substrate presentation. In addition, the hLysoPLA did not display any significant PLA2 activity toward PlsCho and phosphatidylcholine in both mixed-micelle and vesicle forms. Since no significant PLA1, PLA2, acyltransferase, transacylase and esterase activities were found for rat and mouse LysoPLA, we conclude that these enzymes form a group of specific LysoPLAs that recognize and act on only lysophospholipids.

Lysophospholipases are critical enzymes that act on biological membranes to regulate the multifunctional lysophospholipids; increased levels of lysophospholipids are associated with a host of diseases. The instant invention describes the cDNA cloning of a human brain 25 kDa lysophospholipid-specific lysophospholipase (hLysoPLA).

The enzyme (at both mRNA and protein levels) is widely distributed in tissues, but with quite different abundances. The hLysoPLA hydrolyzes lysophosphatidylcholine in both monomeric and micellar forms, and exhibits apparent cooperativity and surface dilution kinetics, but not interfacial activation. Detailed kinetic analysis indicates that the hLysoPLA binds first to the micellar surface and then to the substrate presented on the surface. The kinetic parameters associated with this surface dilution kinetic model are reported, and it is concluded that hLysoPLA has a single substrate binding site and a surface recognition site. The apparent cooperativity observed is likely due to the change of substrate presentation. In contrast to many nonspecific lipolytic enzymes that exhibit lysophospholipase activity, hLysoPLA hydrolyzes only lysophospholipids and has no other significant enzymatic activity. Of special interest, hLysoPLA does not act on plasmenylcholine. Of the several inhibitors tested, only methyl arachidonyl fluorophosphonate (MAFP) potently and irreversibly inhibits the enzymatic activity. The inhibition by MAFP is consistent with the catalytic mechanism proposed for the enzyme—a serine hydrolase with a catalytic triad composed of Ser-119, Asp-174 and His-208.

While the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

What is claimed is:

1. An isolated nucleic acid encoding a lysophospholipid-specific human brain lysophospholipase enzyme protein molecule, comprising the nucleotide sequence of SEQ.ID.No. 1.

2. A recombinant expression vector containing the nucleic acid according to claim 1.

3. An isolated host cell containing the recombinant expression vector of claim 2.

4. A composition comprising the nucleic acid of claim 1 and a pharmaceutically acceptable carrier.

* * * * *

SEQUENCE LISTING

```
<160> NUMBER OF SEQ ID NOS: 6

<210> SEQ ID NO 1
<211> LENGTH: 710
<212> TYPE: DNA
<213> ORGANISM: Homo sapiens

<400> SEQUENCE: 1
atgtgcggca ataacatgtc aacccccgctg cccgccatcg tgcccgccgc ccggaaggcc      60
accgctgcgg tgattttcct gcatggattg ggagatactg ggcacggatg ggcagaagcc     120
tttgcaggta tcagaagttc acatatcaaa tatatctgcc cgcatgcgcc tgttaggcct     180
gttacattaa atatgaacgt ggctatgcct tcatggtttg atattattgg gctttcacca     240
gattcacagg aggatgaatc tgggattaaa caggcagcag aaaatataaa agctttgatt     300
gatcaagaag tgaagaatgg cattccttct aacagaatta ttttgggagg gttttctcag     360
ggaggagctt tatctttata tactgcccctt accacacagc agaaactggc aggtgtcact     420
gcactcagtt gctggcttcc acttcgggct tcccttccac agggtcctat cggtggtgct     480
aatagagata tttctattct ccagtgccac ggggattgtg acccttttggt tcccctgatg     540 tttggttctc ttacggtgga aaaactaaaa acattggtga atccagccaa tgtgaccttt     600
aaaacctatg aaggtatgat gcacagttcg tgtcaacagg aaatgatgga tgtcaagcaa     660
ttcattgata aactcctacc tccaattgat tgacgtcact aagaggcctt                710

<210> SEQ ID NO 2
<211> LENGTH: 230
<212> TYPE: PRT
<213> ORGANISM: Homo sapiens

<400> SEQUENCE: 2

Met Cys Gly Asn Asn Met Ser Thr Pro Leu Pro Ala Ile Val Pro Ala
  1               5                  10                  15

Ala Arg Lys Ala Thr Ala Ala Val Ile Phe Leu His Gly Leu Gly Asp
             20                  25                  30

Thr Gly His Gly Trp Ala Glu Ala Phe Ala Gly Ile Arg Ser Ser His
         35                  40                  45

Ile Lys Tyr Ile Cys Pro His Ala Pro Val Arg Pro Val Thr Leu Asn
     50                  55                  60

Met Asn Val Ala Met Pro Ser Trp Phe Asp Ile Ile Gly Leu Ser Pro
```

-continued

```
                65                  70                  75                  80
Asp Ser Gln Glu Asp Glu Ser Gly Ile Lys Gln Ala Glu Asn Ile
                    85                  90                  95
Lys Ala Leu Ile Asp Gln Glu Val Lys Asn Gly Ile Pro Ser Asn Arg
                100                 105                 110
Ile Ile Leu Gly Gly Phe Ser Gln Gly Gly Ala Leu Ser Leu Tyr Thr
                115                 120                 125
Ala Leu Thr Thr Gln Gln Lys Leu Ala Gly Val Thr Ala Leu Ser Cys
    130                 135                 140
Trp Leu Pro Leu Arg Ala Ser Leu Pro Gln Gly Pro Ile Gly Gly Ala
145                 150                 155                 160
Asn Arg Asp Ile Ser Ile Leu Gln Cys His Gly Asp Cys Asp Pro Leu
                165                 170                 175
Val Pro Leu Met Phe Gly Ser Leu Thr Val Glu Lys Leu Lys Thr Leu
                180                 185                 190
Val Asn Pro Ala Asn Val Thr Phe Lys Thr Tyr Glu Gly Met Met His
                195                 200                 205
Ser Ser Cys Gln Gln Glu Met Met Asp Val Lys Gln Phe Ile Asp Lys
    210                 215                 220
Leu Leu Pro Pro Ile Asp
225                 230

<210> SEQ ID NO 3
<211> LENGTH: 758
<212> TYPE: DNA
<213> ORGANISM: Homo sapiens
<220> FEATURE:
<221> NAME/KEY: CDS
<222> LOCATION: (49)..(741)

<400> SEQUENCE: 3
ccgggcgccc gctcttcctt ccgcttgcgc tgtgagctga ggcggtgt atg tgc ggc        57
                                                    Met Cys Gly
                                                      1 aat aac atg tca acc ccg ctg ccc gcc atc gtg ccc gcc gcc cgg aag       105
Asn Asn Met Ser Thr Pro Leu Pro Ala Ile Val Pro Ala Ala Arg Lys
     5                  10                  15 gcc acc gct gcg gtg att ttc ctg cat gga ttg gga gat act ggg cac       153
Ala Thr Ala Ala Val Ile Phe Leu His Gly Leu Gly Asp Thr Gly His
 20                  25                  30                  35 gga tgg gca gaa gcc ttt gca ggt atc aga agt tca cat atc aaa tat       201
Gly Trp Ala Glu Ala Phe Ala Gly Ile Arg Ser Ser His Ile Lys Tyr
                 40                  45                  50 atc tgc ccg cat gcg cct gtt agg cct gtt aca tta aat atg aac gtg       249
Ile Cys Pro His Ala Pro Val Arg Pro Val Thr Leu Asn Met Asn Val
                 55                  60                  65 gct atg cct tca tgg ttt gat att att ggg ctt tca cca gat tca cag       297
Ala Met Pro Ser Trp Phe Asp Ile Ile Gly Leu Ser Pro Asp Ser Gln
             70                  75                  80 gag gat gaa tct ggg att aaa cag gca gca gaa aat ata aaa gct ttg       345
Glu Asp Glu Ser Gly Ile Lys Gln Ala Ala Glu Asn Ile Lys Ala Leu
         85                  90                  95 att gat caa gaa gtg aag aat ggc att cct tct aac aga att att ttg       393
Ile Asp Gln Glu Val Lys Asn Gly Ile Pro Ser Asn Arg Ile Ile Leu
100                 105                 110                 115 gga ggg ttt tct cag gga gga gct tta tct tta tat act gcc ctt acc       441
Gly Gly Phe Ser Gln Gly Gly Ala Leu Ser Leu Tyr Thr Ala Leu Thr
                120                 125                 130
```

```
aca cag cag aaa ctg gca ggt gtc act gca ctc agt tgc tgg ctt cca      489
Thr Gln Gln Lys Leu Ala Gly Val Thr Ala Leu Ser Cys Trp Leu Pro
            135                 140                 145 ctt cgg gct tcc ctt cca cag ggt cct atc ggt ggt gct aat aga gat      537
Leu Arg Ala Ser Leu Pro Gln Gly Pro Ile Gly Gly Ala Asn Arg Asp
        150                 155                 160 att tct att ctc cag tgc cac ggg gat tgt gac cct ttg gtt ccc ctg      585
Ile Ser Ile Leu Gln Cys His Gly Asp Cys Asp Pro Leu Val Pro Leu
165                 170                 175 atg ttt ggt tct ctt acg gtg gaa aaa cta aaa aca ttg gtg aat cca      633
Met Phe Gly Ser Leu Thr Val Glu Lys Leu Lys Thr Leu Val Asn Pro
180                 185                 190                 195 gcc aat gtg acc ttt aaa acc tat gaa ggt atg atg cac agt tcg tgt      681
Ala Asn Val Thr Phe Lys Thr Tyr Glu Gly Met Met His Ser Ser Cys
                200                 205                 210 caa cag gaa atg atg gat gtc aag caa ttc att gat aaa ctc cta cct      729
Gln Gln Glu Met Met Asp Val Lys Gln Phe Ile Asp Lys Leu Leu Pro
            215                 220                 225 cca att gat tga cgtcactaag aggcctt                                    758
Pro Ile Asp
        230

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggggggcata tgtgcggcaa taacatgtca acccc                                35

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcgcgaattc tcaatcaatt ggaggtagga gtttat                               36

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Gly Ser Ser His His His His His His Ser Ser Gly Leu Val Pro
 1               5                  10                  15

Arg Gly Ser His
            20
```